United States Patent [19]

Dostert et al.

[11] 4,250,318

[45] Feb. 10, 1981

[54] NOVEL 5-HYDROXYMETHYL OXAZOLIDINONES, THE METHOD OF PREPARING THEM AND THEIR APPLICATION IN THERAPEUTICS

[75] Inventors: Philippe L. Dostert, Chaville; Colette A. Douzon, Paris; Guy R. Bourgery, Colombes; Claude G. Gouret, Meudon; Gisele C. Mocquet, Paris; Jean-Alain Coston, Garches, all of France

[73] Assignee: Delalande S.A., Courbevoie, France

[21] Appl. No.: 932,212

[22] Filed: Aug. 9, 1978

[30] Foreign Application Priority Data

Aug. 26, 1977 [FR] France ............................. 77 26105
May 23, 1978 [FR] France ............................. 78 15342

[51] Int. Cl.$^3$ ................... C07D 263/24; A61K 31/42
[52] U.S. Cl. ............................... 548/229; 548/232; 546/277; 544/336; 544/139
[58] Field of Search .................... 260/307 C; 548/229, 548/232

[56] References Cited

U.S. PATENT DOCUMENTS

3,654,298  4/1972  Douzon et al. .................. 548/232
3,655,687  4/1972  Fauran et al. .................. 260/307 C

*Primary Examiner*—Donald G. Daus
*Assistant Examiner*—D. B. Springer
*Attorney, Agent, or Firm*—Blanchard, Flynn, Thiel, Boutell & Tanis

[57] ABSTRACT

There are disclosed 3-substituted phenyl-5-hydroxymethyl oxazolidinones which possess anti-depressant properties. The compounds are prepared by cyclizing, with ethyl carbonate, 1-substituted phenylamino-2,3-propanediol compounds.

8 Claims, No Drawings

NOVEL 5-HYDROXYMETHYL OXAZOLIDINONES, THE METHOD OF PREPARING THEM AND THEIR APPLICATION IN THERAPEUTICS

The present invention concerns novel 5-hydroxymethyl oxazolidinones, the method of preparing them and their application in therapeutics.

The compounds in question correspond more exactly to the formula:

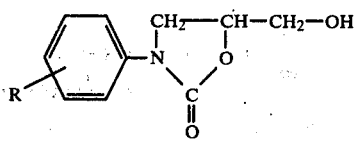

in which R represents:
(1) an m-dimethylamino; p-n pentylamino; p-trifluoromethyl; p-phenoxymethyl group whose phenyl nucleus may be substituted in position 3 by a nitro group; p-(m-chlorophenylethyl) or p-styryl (trans) group;
(2) an —$SR_1$ group situated in para position and in which $R_1$ represents an alkyl group having 5 carbon atoms or an acetylmethylthio group;
(3) an —$OR_2$ group situated in para position in which $R_2$ represents:
an isopentyl, neopentyl, 3,3-dimethylbutyl or 2-ethylbutyl group,
a cycloalkylmethyl group in which the cycloalkyl group comprises from 3 to 7 carbon atoms or a cycloalkylethyl group in which the cycloalkyl group comprises 5 or 6 carbon atoms,
a pentene-4 yl group,
a 1-cycloalkene methyl group comprising 6 or 7 carbon atoms, a 1-methyl cyclopentylmethyl or 1,4-cyclohexadiene methyl group, or
a 1,3-dioxolan-2-yl methyl; 1,3-diotholanne-2 yl methyl; 1,3-oxathiolan-2-yl methyl; 1,3-dithian-2-yl methyl; tetrahydropyran-2-yl methyl; tetrahydropyran-3-yl methyl; or tetrahydropyran-4 yl methyl group;
(4) a substituted benzyloxy group situated in para position and of formula:

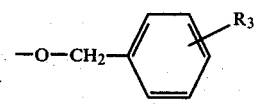

in which $R_3$ represents an element chosen from the following: o-cyano, m-chloro, m-bromo, m-iodo, m-nitro, m-cyano, p-acetamido, m-amino, p-$NHCOOCH_3$, p-$NHCOC_2H_5$;
(5) a disubstituted benzyloxy group situated in para position and of formula:

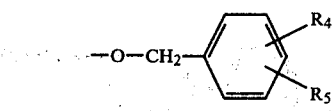

in which the couple ($R_4$, $R_5$) assumes a value chosen from the following: (3—Cl, 4—Cl), (2—Cl, 4—Cl), (3—Cl, 5—Cl), (3—Cl, 4—F), (3—$NO_2$, 4—Cl), (3—Cl, 4—$NO_2$), (3—CN, 4—F), (3$NO_2$, 4—F), (3—$NO_2$, 5—CN), (3—$NO_2$, 5—Cl);
(6) an heterocyclic methyloxy chain situated in para position and of formula:

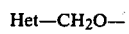

Het—$CH_2O$— in which Het represents one of the following radicals: 2-pyridyl, 3-pyridyl, 4-pyridyl, 2-thienyl, 3-thienyl, 2-furyl, 3-furyl, 2-pyrazinyl;
(7) a —$COR_6$ chain situated in para position and in which $R_6$ represents an alkyl group comprising from 2 to 3 carbon atoms;
(8) an —O—$CH_2$—CO—$R_7$ chain situated in meta or para position and in which $R_7$ represents an alkyl group comprising from 1 to 3 carbon atoms;
(9) an —O—$(CH_2)_n$—CN chain situated in meta or para position and in which n is equal to 1, 2, 3 or 4; or
(10) a chain situated in para position chosen from the following: methoxymethyloxy, 2-morpholino ethoxy; acetylmethyloxy oxime.

The compounds of formula (I) are obtained:
(a) by cyclizing through the action of ethyl carbonate preferably in the presence of a base and an organic solvent, a 1-phenylamino 2,3-propanediol of formula:

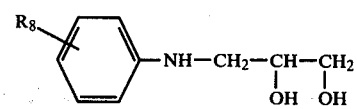

in which $R_8$ represents:
an m-dimethylamino, p-phenoxymethyl, p-trifluoromethyl, p-(m-chlorophenylethyl) or p-styryl (trans) group,
an —$SR_1$ group situated in para position and in which $R_1$ represents an alkyl group comprising 5 carbon atoms, or
a —$COR_6$ chain situated in para position and in which $R_6$ represents an alkyl group comprising from 2 to 3 carbon atoms, which leads to compounds of formula:

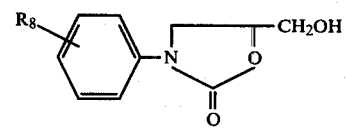

where $R_8$ has the same meaning as above;
(b) by cyclizing, through the action of ethyl carbonate, 1-phenylamino 2,3-propanediol of formula:

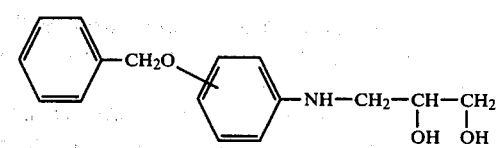

which leads to the compound of formula:

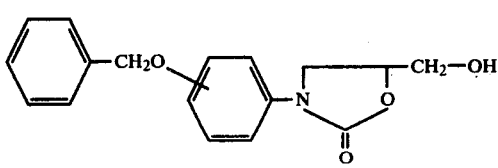
(IV)

which is then subjected to the action of hydrogenolysis in alcohol in the presence of palladium on charcoal, to obtain the compound of formula:

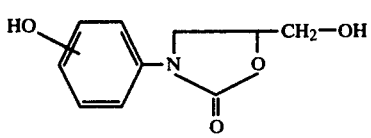
(V)

which is condensed, preferably to reflux in acetone or acetonitrile and in the presence of potassium carbonate, with a product corresponding to one of the following formulae:

$R_9$—Cl (VI)
$R_9$—Br (VII)

(VIII)

in which $R_9$:
has the same significance as $R_2$ in formula (I) except the 1,3-dithiola-2-yl methyl; 1,3-oxathiolan-2-yl methyl and 1,3-dithian-2-yl methyl groups, or
represents:
a substituted benzyl group of formula:

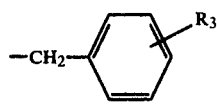

where $R_3$ has the same significance as in formula (I),
a disubstituted benzyl group of formula:

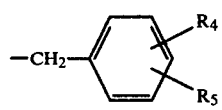

where $R_4$ and $R_5$ have the same significance as in formula (I),
an heterocyclic methyl chain of formula:

Het-CH$_2$— where Het has the same significance as in formula (I),
a —CH$_2$—CO—$R_7$ chain in which $R_7$ has the same significance as in formula (I), or
a group chosen from the following: methoxymethyl, 2-morpholino ethyl, cyanomethyl, 3-cyano propyl, 4-cyano butyl; which leads to the compounds of formula:

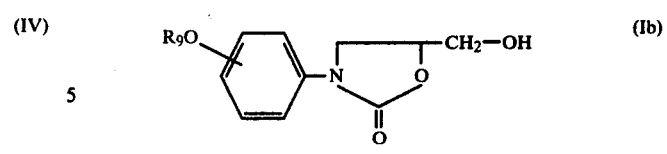
(Ib)

where $R_9$ has the same significance as above;
(c) by cyclizing, through the action of ethyl carbonate, 1-phenylamino 2,3-propanediol of formula:

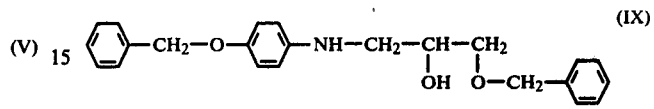
(IX)

which leads to the novel compound of formula:

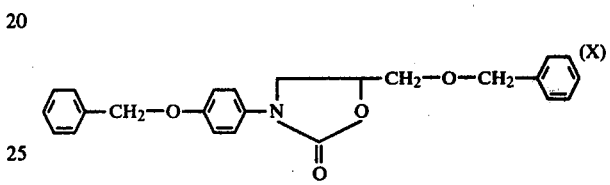
(X)

which is subjected to selective hydrogenolysis in ethanol in the presence of palladium on charcoal, preferably at room temperature, to provide the novel compound of formula:

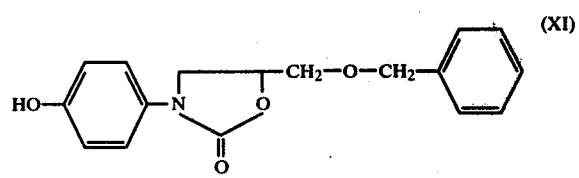
(XI)

which is condensed with acrylonitrile of formula:

CH$_2$=CH—CN (XII)

in the presence of triton B, which leads to the novel compound of formula:

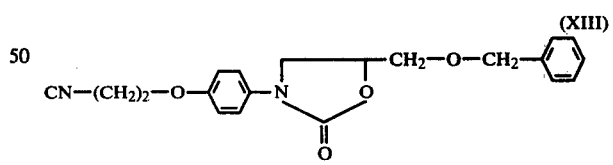
(XIII)

which is then hydrogenolysed in ethanol in the presence of palladium on charcoal and preferably of a few drops of hydrochloric ethanol, to obtain the compound of formula:

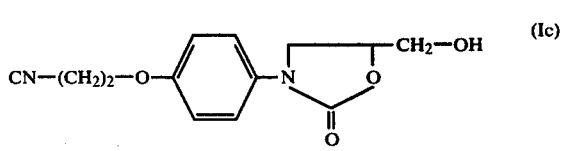
(Ic)

(a) by condensing the compound of formula:

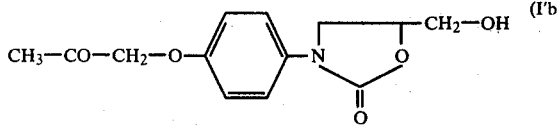 (I'b)

obtained at point (b) above, with hydroxylamine hydrochloride in aqueous ethanol, which leads to the compound of formula:

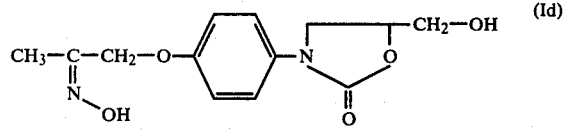 (Id)

(e) by cyclizing, through the action of ethyl carbonate, the compound of formula:

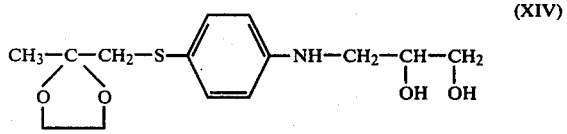 (XIV)

which leads to the novel compound of formula:

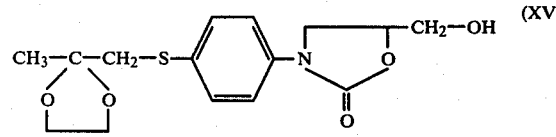 (XV)

which is then hydrolyzed in the presence of concentrated hydrochloric acid in tetrahydrofuran, to obtain the compound of formula:

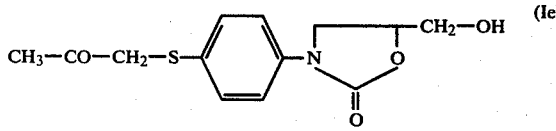 (Ie)

(f) by cyclizing, through the action of ethyl carbonate, the compound of formula:

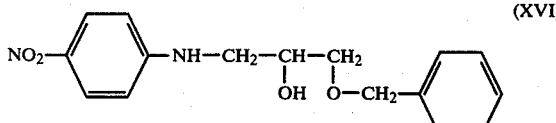 (XVI)

which leads to the novel compound of formula:

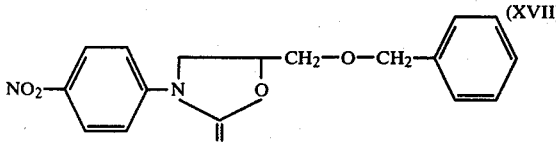 (XVII)

which is then subjected to simultaneous reduction and hydrogenolysis, in ethanol in the presence of palladium on charcoal and preferably of hydrochloric ethanol 6,5 N to obtain the novel compound of formula:

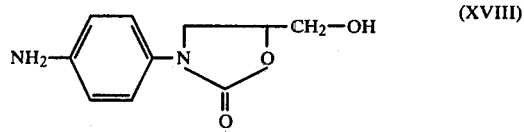 (XVIII)

which is condensed with the n-pentyl bromide of formula:

$C_5H_{11}n-Br$ (XIX)

in butanol in the presence of potassium carbonate, which leads to the compound of formula:

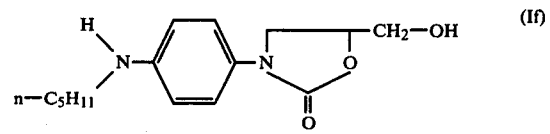 (If)

(g) by cyclizing the compound of formula:

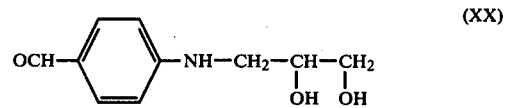 (XX)

in the presence of ethyl carbonate, particularly in dioxane, by subjecting the compound thus obtained of formula:

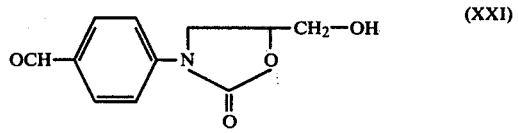 (XXI)

to the action of the tert butyric acid chloride, particularly in pyridine, by reducing the resulting compound of formula:

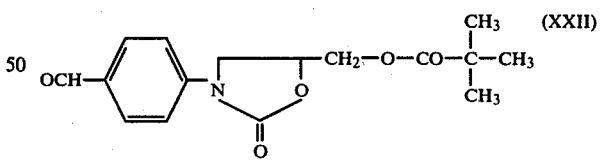 (XXII)

with sodium borohydride, particularly in methanol, and by subjecting the compound obtained of formula:

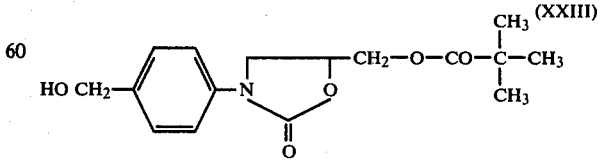 (XXIII)

to the action of methyl chloride, particularly in methylene chloride, which leads to the compound of formula:

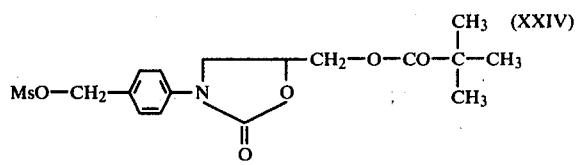

where Ms represents the mesyl radical, which is reacted with metanitrophenol in the presence of sodium hydride, the compound obtained of formula:

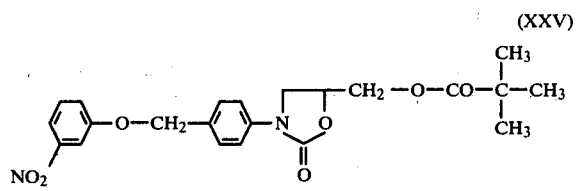

being hydrolyzed, preferably in the presence of a base such as potash, particularly in methanol, which leads to the compound of formula:

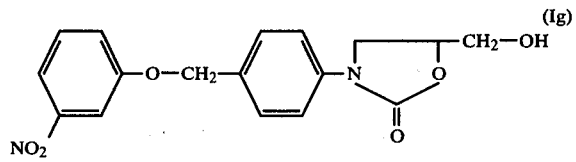

and, (h) by condensing diethylacetal bromoacetaldehyde of formula:

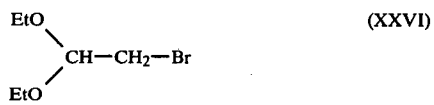

on 3-p-hydroxyphenyl 5-hydroxymethyl 2-oxazolidinone of formula (V') obtained in accordance with point (b) above, in the presence of sodium hydride and an organic solvent such as DMF for example, the resulting compound of formula:

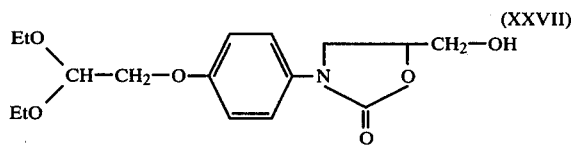

being reacted with a compound of formula:

in which the couple (n, X) may assume the following values: (1, sulfur), (1, oxygen), (2, sulfur), preferably in the presence of boron trifluoride etherate in methylene chloride, which leads to the compounds of formula:

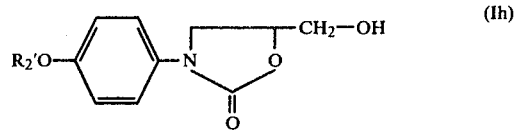

where $R'_2$ designates a 1,3-dithiolan-2-yl methyl; 1,3-oxathiolan-2-yl methyl; or 1,3-dithian-2-yl methyl group.

The compounds of formula (II) are, for their part, obtained by condensation in methanol or ethanol of anilines of formula:

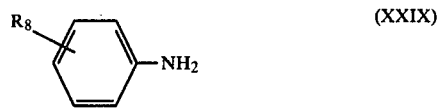

in which $R_8$ has the same significance as in formula (II), with glycidol of formula:

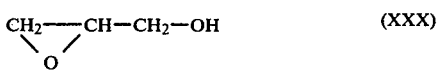

The compounds of formulae (III), (IX), (XIV) and (XVI) are prepared by the same method but using the corresponding anilines.

It should further be noted that the compounds of formulae (I), (XV) and (XVIII) will be regrouped, in the claims, under formula (I').

The examples below are given by way of illustration of the invention.

EXAMPLE 1

5-hydroxymethyl 3-p-trifluoromethylphenyl 2-oxazolidinone (I)—Code number 770 152

A mixture of 46 g (0.195 mole) of 3-paratrifluoromethylphenylamino 1,2-propanediol (II), 23.6 g (0.2 mole) of ethyl carbonate and a few drops of a 5% methanolic solution of soda methylate in 400 ml of toluene were heated at 105° C. for an hour. Then, the solvents were evaporated and the residue chromatographed on a silica column (eluent:CHCl₃), this operation being followed by recrystallization in isopropyl ether.

Yield: 20%.
Melting point: 88° C.
Empirical formula: $C_{11}H_{10}F_3NO_3$.
Molecular weight: 261,19.

| Elementary analysis: | C | H | N |
|---|---|---|---|
| Calculated (%) | 50.58 | 3.86 | 5.36 |
| Obtained (%) | 50.74 | 3.83 | 5.32 |

The compounds with the following code numbers and shown in Table I below can be obtained in the same way: 770 365-770 423-770 696-770 180-770 155-771 181-780 564.

EXAMPLE 2

5-hydroxymethyl 3-meta-cyanomethyloxyphenyl 2-oxazolidinone—Code number: 770 231

1st step: 5-hydroxymethyl 3-m-hydroxyphenyl 2-oxazolidinone (V)

A solution of 132.5 g (0.44 mole) of 5-hydroxymethyl 3-m-benzyloxyphenyl 2-oxazolidinone prepared by an operational mode similar to that of example 1, in 1.5 liter of alcohol in the presence of 13 g of palladium on 10% charcoal was hydrogenolized in an autoclave, between 45° and 50° C., at a pressure of 2 kg for 6 hours. The solution was filtered and the filtrate evaporated and recrystallized in isopropyl alcohol.

2nd step: 5-hydroxymethyl 3-m-cyanomethyloxyphenyl 2-oxazolidinone—Code number 770 231

A mixture of 15 g (0.07 mole) of 5-hydroxymethyl 3-m-hydroxyphenyl 2-oxazolidinone prepared in the previous step, 7.6 g (0.1 mole) of chloroacetonitrile, 38 g (0.28 mole) of potassium carbonate and 1 g of potassium iodide in 450 ml of acetone was brought to reflux for 8 hours. The mixture was filtered, the filtrate was evaporated and the residue was recrystallized in absolute alcohol.

Yield: 71%.
Melting point: 110° C.
Empirical formula: $C_{12}H_{12}N_2O_4$.
Molecular weight: 248,23.

| Elementary analysis: | C | H | N |
|---|---|---|---|
| Calculated (%) | 58.06 | 4.87 | 11.29 |
| Obtained (%) | 58.08 | 4.90 | 11.35 |

In the same way the compounds, shown in table I below, with the following code numbers can be obtained: 770 388-770 788-770 467-770 466-770 196-770 154-760 904-750 601-760 557-770 234-770 318-770 222-770 569-770 268-770 354-770 416-770 572-770 672-770 790-770 789-770 298-770 221-770 299-770 673-770 845-770 230-770 889-771 082-771 249-;b 771 246-771 197-780 030-771 245-770 949-780 076-770 984-770 962-780 034-770 900-771 301-771 321-771 240-780 182-780 443-770 955-771 125-771 199-770 979-771 067-780 259-780 562.

EXAMPLE 3:

3-(2-paracyano ethoxyphenyl) 5-hydroxymethyl 2-oxazolidinone Code number: 770 131

1st step: 3-(p-benzyloxyphenyl) 5-benzyloxymethyl 2-oxazolidinone—Code number: 760 431

This compound is prepared by using a method identical to that of example 1, from the appropriate propanediol:

Yield: 80%.
Melting point: 126° C.
Empirical formula: $C_{24}H_{23}NO_4$.
Molecular weight: 389,43.

| Elementary analysis: | C | H | N |
|---|---|---|---|
| Calculated (%) | 74.02 | 5.95 | 3.60 |
| Obtained (%) | 73.87 | 6.1 | 3.89 |

2nd step: 3-(p-hydroxyphenyl) 5-benzyloxymethyl 2-oxazolidinone—Code number: 760 484

A suspension of 18 g (0.046 mole) of the compound prepared in the previous steps and 2 g of palladium on 10% charcoal in 400 ml of absolute alcohol was hydrogenolized in an autoclave, at room temperature, under a pressure of 4 to 5 kg of hydrogen. Then, it was filtered, the solvent evaporated and recrystallized in absolute alcohol.

Yield: 73%.
Melting point: 153° C.
Empirical formula: $C_{17}H_{17}NO_4$.

| Elementary analysis: | C | H | N |
|---|---|---|---|
| Calculated (%) | 68.21 | 5.73 | 4.68 |
| Obtained (%) | 68.38 | 5.62 | 4.46 |

3rd step: 3-(2-p-cyanoethoxy phenyl) 5-benzyloxymethyl 2-oxazolidinone—Code number: 760 993

A solution of 13 g (0.03 mole) of the compound prepared in the previous step, in 45 g (0.86 mole) of acrylonitrile in the presence of 1 ml of triton B (40% in methanol) was brought to reflux for 15 hours. Then, the excess acrylonitrile was evaporated, the residue was taken up in 100 ml of NaOH N, filtered, the precipitate was washed in water than in ether and recrystallized in methanol.

Yield: 60%.
Melting point: 112° C.
Empirical formula: $C_{20}H_{20}N_2O_4$.

| Elementary analysis: | C | H | N |
|---|---|---|---|
| Calculated (%) | 68.17 | 5.72 | 7.95 |
| Obtained (%) | 67.89 | 5.66 | 8.21 |

4th step: 3-(2-p-cyano ethoxyphenyl) 5-hydroxymethyl 2-oxazolidinone—Code number: 770 131

A suspension of 3.5 g (0.01 mole) of 3-(2-p-cyanoethoxyphenyl) 5-benzyloxymethyl 2-oxazolidinone prepared in the preceeding step, 0.4 g of palladium on 10% charcoal and 0.05 ml of hydrochloric ethanol 7.5 N, in 250 ml of dioxanne was hydrogenolized in an autoclave at a pressure of 1 kg of hydrogen and at room temperature. It was filtered and the residue was purified by chromatography on a silica column. Eluated by the 50/50 chloroform-acetone mixture, then recrystallized in absolute alcohol; 1 g of expected product was obtained.

Yield: 39%.
Melting point: 131° C.
Empirical formula: $C_{13}H_{14}N_2O_4$.

| Elementary analysis | C | H | N |
|---|---|---|---|
| Calculated (%) | 59.53 | 5.38 | 10.68 |
| Obtained (%) | 59.06 | 5.24 | 10.37 |

EXAMPLE 4:

oxime of 3-(p-acetylmethyloxyphenyl) 5-hydroxymethyl 2-oxazolidinone—Code number: 770 126

A solution of 7 g (0.026 mole) of 3-(p-acetylmethyloxy) 5-hydroxymethyl 2-oxazolidinone (code number 760 652) prepared in accordance with example 2, and 2.1 g (0.03 mole) of hydroxylamine hydrochloride, in a mixture of 120 ml of ethanol and 6 ml of water was maintained for 2 hours at room temperature. Then the solvent was evaporated, the residue was taken up in water, filtered and recrystallized in 96° alcohol.

Yield: 75%.
Melting point: 164° C.
Empirical formula: $C_{13}H_{16}N_2O_5$.

| Elementary analysis: | C | H | N |
|---|---|---|---|
| Calculated (%) | 55.71 | 5.75 | 10.00 |
| Obtained (%) | 55.44 | 5.70 | 10.09 |

EXAMPLE 5:

3-(p-acetylmethylthiophenyl) 5-hydroxymethyl 2-oxazolidinone Code number: 770 501

1st step: 2-methyl p-[3-(5-hydroxymethyl oxazolidinone)]2-phenylmercapto 1,3-dioxan—Code number: 770 500

This compound is prepared by using an operational mode identical with that of example 1 from appropriate propanediol.

Melting point: 140° C.
Empirical formula: $C_{15}H_{19}NO_5S$.

| Elementary analysis: | C | H | N |
|---|---|---|---|
| Calculated (%) | 55.37 | 5.89 | 4.31 |
| Obtained (%) | 55.36 | 5.79 | 4.09 |

2nd step: 3-(p-acetylmethylthiophenyl) 5-hydroxymethyl 2-oxazolidinone—Code number: 770 501

A solution of 10.5 g (0.032 mole) of the compound prepared in the preceeding step in 200 ml of tetrahydrofurane and 10 ml of hydrochloric acid were brought to reflux for 30 minutes. Then, the solvent was evaporated and the residue was taken up in water filtered and recrystallized in methanol.

Yield: 53%.
Melting point: 116° C.
Empirical formula: $C_{13}H_{15}NO_4S$.

| Elementary analysis: | C | H | N |
|---|---|---|---|
| Calculated (%) | 55.50 | 5.37 | 4.98 |
| Obtained (%) | 55.32 | 5.33 | 4.68 |

EXAMPLE 6:

3-p-n pentylaminophenyl 5-hydroxymethyl 2-oxazolidinone Code number: 770 328

1st step: 5-benzyloxymethyl 3-p-nitrophenyl 2-oxazolidinone—Code number: 770 151

This compound is obtained by using an operational mode identical to that of example 1, from appropriate propanediol.

Yield: 78%.
Melting point: 125° C.
Empirical formula: $C_{17}H_{16}N_2O_5$.

| Elementary analysis: | C | H | N |
|---|---|---|---|
| Calculated (%) | 62.19 | 4.91 | 8.53 |
| Obtained (%) | 61.84 | 4.87 | 8.57 |

2nd step: 3-p-aminophenyl 5-hydroxymethyl 2-oxazolidone hydrochloride—Code number: 770 221

A suspension of 25 g (0.076 mole) of the compound prepared in the preceding step, 2.5 g of palladium on 10% charcoal and 12.5 ml of hydrochloric ethanol 6.5 N in 600 ml of absolute ethanol were brought to 50° C., in an autoclave, at a pressure of 3 kg of hydrogen for 2 hours. Then it was filtered, the solvent was evaporated and the residue recrystallized in methanol.

Yield: 64%.
Melting point: 200° C.
Empirical formula: $C_{10}H_{13}ClN_2O_3$.

| Elementary analysis: | C | H | N |
|---|---|---|---|
| Calculated (%) | 49.09 | 5.36 | 11.23 |
| Obtained (%) | 48.63 | 5.27 | 11.25 |

3rd step: 3-p-n pentylaminophenyl 5-hydroxymethyl 2-oxazolidinone Code number: 770 328

A suspension of 6.1 g (0.025 mole) of the compound prepared in the preceding step, 4.5 g (0.03 mole) of n-pentyl bromide, 10 g of potassium carbonate and 0.1 g of sodium iodide in 100 ml of butanol was brought to reflux for 12 hours. It was filtered, the solvent was evaporated and crystallized in a mixture of ether and isopropyl alcohol.

Yield: 10%.
Melting point: 124° C.
Empirical formula: $C_{15}H_{22}N_2O_3$.

| Elementary analysis: | C | H | N |
|---|---|---|---|
| Calculated (%) | 64.72 | 7.97 | 10.07 |
| Obtained (%) | 64.47 | 7.97 | 10.02 |

EXAMPLE 7

3-para (metanitrophenoxymethyl) phenyl 5-hydroxymethyl 2-oxazolidinone—Code number: 771 263

1st step: 3-paraformylphenyl 5-hydroxymethyl 2-oxazolidinone Code number: 770 054

A mixture of 65.4 g of 3-paraformylanilino 1,2-propanediol, 43.6 g of diethyl carbonate and 16 ml of sodium methylate (10% solution in methanol) in 830 ml of dioxan was brought to reflux (by distilling the alcohol formed). Then it was filtered, the filtrate evaporated and the residue taken up in chloroform and washed with a dilute hydrochloric acid solution. Then, it was dried, the solvent evaporated and the residue chromatographed on a silica column, which gave the product desired.

Yield: 23%.
Melting point: 123° C.
Empirical formula: $C_{11}H_{11}NO_4$.
Molecular weight: 221,21.

| Elementary analysis: | C | H | N |
|---|---|---|---|
| Calculated (%) | 59.72 | 5.01 | 6.33 |
| Obtained (%) | 59.49 | 4.66 | 6.20 |

2nd step: 3-paraformylphenyl ter-butylcarbonyloxymethyl 2-oxazolidinone Code number: 771 213

To a solution of 15.5 g of the compound prepared in the preceding stage in 180 ml of pyridine, there was slowly added 12.2 ml of tert-butyric acid chloride. After 1 hour at room temperature, it was diluted with water and the precipitate formed was filtered, dried and recrystallized in ethanol.

Yield: 90%.
Melting point: 134° C.
Empirical formula: $C_{16}H_{19}NO_5$.

Molecular weight: 305,32.

| Elementary analysis: | C | H | N |
|---|---|---|---|
| Calculated (%) | 62.94 | 6.27 | 4.59 |
| Obtained (%) | 62.64 | 6.57 | 4.46 |

3rd step: 3-para-hydroxymethylphenyl 5-tert-butylcarbonyloxymethyl 2-oxazolidinone Code number: 771 214

To a suspension of 11.3 g of the compound prepared in the preceding stage there was slowly added 0.7 g of sodium borohyrdride. After 10 minutes, the solvent was evaporated, the residue was taken up in ethyl acetate, washed with water and dried, the solvent was evaporated and the residue was recrystallized in a mixture of ether and isopropanol.
Yield: 80%.
Melting point: 102° C.
Empirical formula: $C_{16}H_{21}NO_5$.
Molecular weight: 307,34.

| Elementary analysis: | C | H | N |
|---|---|---|---|
| Calculated (%) | 62.52 | 6.89 | 4.56 |
| Obtained (%) | 62.58 | 7.01 | 4.32 |

4th step: 3-para (metanitrophenoxymethyl) phenyl 5-hydroxymethyl 2-oxazolidinone—Code number: 771 263

To a solution of 11.7 g of the compound obtained in the preceding step in 150 ml of methylene chloride there was added 10.6 ml of triethylamine and 6 ml of mesyl chloride, at 0° C. Then, after 3 hours contact at room temperature, it was diluted with water, decanted and the organic phase evaporated. The residue obtained (dissolved in 100 ml of dimethylformamide) was added to a solution of 3.7 g of metanitrophenol and 1.25 g of sodium hydride (at 50%) in 50 ml of dimethylformamide and the mixture was brought to 60° C. for 3 hours. Then, the mixture was poured into water, extracted with ethyl acetate and dried; the solvent was evaporated and the residue was treated with a solution of 0.6 g of potash in 120 ml of methanol. After 1 hour of reflux, the mixture was poured into water and the precipitate obtained was filtered and then recrystallized in methanol, then in ethanol.
Yield: 44%.
Melting point: 142° C.
Empirical formula: $C_{17}H_{16}N_2O_6$.
Molecular weight: 344,31.

| Elementary analysis: | C | H | N |
|---|---|---|---|
| Calculated (%) | 59.30 | 4.68 | 8.14 |
| Obtained (%) | 59.44 | 4.38 | 7.99 |

EXAMPLE 8

3-para-[(1,3-dithiolan-2yl)methoxy]phenyl 5-hydroxymethyl 2-oxazolidinone—Code number: 780 080

1st step: 3-para (2,2diethoxy) ethoxyphenyl 5-hydroxymethyl 2-oxazolidinone.—Code number: 771 049

To a solution of 21 g of 3-para-hydroxy-phenyl-5-hydroxymethyl 2-oxazolidnone in 200 ml of dimethylformamide was added 4.8 g of sodium hydride (at 50%) then 30 ml of acetal diethyl bromoacetaldehyde. The mixture was brought to 50° C. for 13 hours, then it was poured into chilled water, extracted with ethyl acetate, washed with water, the solvent was evaporated and the residue chromarographed on a silica column. Eluated with the mixture 99% $CHCl_3$-1% $CH_3OH$, 17 g of the desired product were obtained.
Melting point: 90° C.
Empirical formula: $C_{16}H_{23}NO_6$.
Molecular weight: 325,35.

| Elementary analysis: | C | H | N |
|---|---|---|---|
| Calculated (%) | 59.06 | 7.13 | 4.31 |
| Obtained (%) | 58.82 | 7.15 | 4.22 |

2nd step: 3-para[(1,3-dithiolan-2-yl)-methoxy]phenyl 5-hydroxymethyl 2-oxazolidinone—Code number: 780 080

A solution of 2.9 g of the compound prepared in the preceding step, 1.2 ml of 1,2-ethanedithiol and 1 ml of boron trifluoride etherate in 35 ml of methylene chloride is maintained at room temperature during 45 mn. Then, it was diluted with ether and the precipitate formed was filtered.
Yield: 60%.
Melting point: 160° C.
Empirical formula: $C_{14}H_{17}NO_4S_2$.
Molecular weight: 327,42.

| Elementary analysis: | C | H | N |
|---|---|---|---|
| Calculated (%) | 51.35 | 5.23 | 4.28 |
| Obtained (%) | 51.51 | 5.28 | 4.00 |

By using the same process but from the corresponding reagents, the compounds with code numbers 780 077 and 780 112, shown in Table 1 below, were obtained.

TABLE I

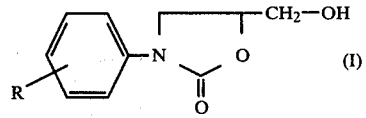

(I)

| Code number | R | Empirical formula | Molecular weight | Melting point (°C.) | Yield (%) | Calculated (%) C | H | N | Obtained (%) C | H | N |
|---|---|---|---|---|---|---|---|---|---|---|---|
| 77 0365 | 4-CO—Et | $C_{13}H_{15}NO_4$ | 249,26 | 186 | 62 | 62,64 | 6,07 | 5,62 | 62,87 | 6,25 | 5,41 |
| 77 0423 | 4-$COC_3H_7n$ | $C_{14}H_{17}NO_4$ | 263,28 | 120 | 68 | 63,86 | 6,51 | 5,32 | 63,75 | 6,67 | 5,20 |
| 77 0152 | 4 $CF_3$ | $C_{11}H_{10}F_3NO_3$ | 261,19 | 88 | 20 | 50,58 | 3,86 | 5,36 | 50,74 | 3,83 | 5,32 |

TABLE I-continued $$\text{(I)} \quad R-\underset{}{\underset{}{\text{C}_6\text{H}_4}}-N\underset{\underset{O}{\|}}{\overset{\text{CH}_2-\text{OH}}{\underset{}{\big|}}}\underset{}{\text{O}}$$

| Code number | R | Empirical formula | Molecular weight | Melting point (°C.) | Yield (%) | Calculated (%) C | H | N | Obtained (%) C | H | N |
|---|---|---|---|---|---|---|---|---|---|---|---|
| 77 0696 | 4-O-CH$_2$-C$_6$H$_5$ | C$_{17}$H$_{17}$NO$_4$ | 299,31 | 140 | 10 | 68,21 | 5,73 | 4,68 | 68,22 | 5,57 | 4,85 |
| 77 0388 | 4-O CH$_2$-cyclopropyl | C$_{14}$H$_{17}$NO$_4$ | 263,28 | 134 | 76 | 63,86 | 6,51 | 5,32 | 63,91 | 6,57 | 5,30 |
| 77 0788 | 4 O-CH$_2$-cyclobutyl | C$_{15}$H$_{19}$NO$_4$ | 277,31 | 108 | 48 | 64,96 | 6,91 | 5,05 | 64,66 | 6,89 | 4,94 |
| 77 0467 | 4 O-CH$_2$-cyclopentyl | C$_{16}$H$_{21}$NO$_4$ | 291,34 | 130 | 30 | 65,96 | 7,27 | 4,81 | 66,04 | 7,24 | 4,53 |
| 77 0466 | 4-O-CH$_2$-cyclopentenyl | C$_{16}$H$_{19}$NO$_4$ | 289,32 | 119 | 81 | 66,42 | 6,62 | 4,84 | 66,14 | 6,44 | 4,84 |
| 77 0196 | 4 O-(CH$_2$)$_3$-CH=CH$_2$ | C$_{15}$H$_{19}$NO$_4$ | 277,31 | 102 | 51 | 64,96 | 6,91 | 5,05 | 64,93 | 7,00 | 5,18 |
| 77 0154 | 4 O CH$_2$-CO-CH(CH$_3$)$_2$ | C$_{15}$H$_{19}$NO$_5$ | 293,31 | 137 | 58 | 61,42 | 6,53 | 4,78 | 61,27 | 6,56 | 4,66 |
| 77 0131 | 4 O(CH$_2$)$_2$-CN | C$_{13}$H$_{14}$N$_2$O$_4$ | 262,26 | 131 | 39 | 59,53 | 5,38 | 10,68 | 59,06 | 5,24 | 10,37 |
| 77 0126 | 4-O-CH$_2$-C(=N-OH)-CH$_3$ | C$_{13}$H$_{16}$N$_2$O$_5$ | 280,27 | 164 | 75 | 55,71 | 5,75 | 10,00 | 55,44 | 5,70 | 10,09 |
| 77 0501 | 4-S CH$_2$ CO CH$_3$ | C$_{13}$H$_{15}$NO$_4$S | 281,32 | 116 | 55 | 55,50 | 5,37 | 4,98 | 55,32 | 5,33 | 4,68 |
| 77 0328 | 4-NH-C$_5$H$_{11}$n | C$_{15}$H$_{22}$N$_2$O$_3$ | 278,34 | 124 | 10 | 64,72 | 7,97 | 10,07 | 64,47 | 7,97 | 10,02 |
| 77 0155 | 3-N(CH$_3$)$_2$ | C$_{12}$H$_{16}$N$_2$O$_3$ | 236,26 | 110 | 60 | 61,00 | 6,83 | 11,86 | 61,02 | 6,76 | 11,75 |
| 77 0230 | 3-OCH$_2$ CO CH$_3$ | C$_{13}$H$_{15}$NO$_5$ | 265,26 | 102 | 53 | 58,86 | 5,70 | 5,28 | 58,61 | 5,78 | 5,27 |
| 77 0231 | 3-O CH$_2$ CN | C$_{12}$H$_{12}$N$_2$O$_4$ | 248,23 | 110 | 71 | 58,06 | 4,87 | 11,29 | 58,08 | 4,90 | 11,35 |
| 760557 | 4-O-CH$_2$-C$_6$H$_4$-Br | C$_{17}$H$_{16}$BrNO$_4$ | 378,27 | 136 | 70 | 53,98 | 4,26 | 3,70 | 54,07 | 4,25 | 3,71 |
| 77 0234 | 4-O-CH$_2$-C$_6$H$_4$-NO$_2$ | C$_{17}$H$_{16}$N$_2$O$_6$ | 344,31 | 135 | 55 | 59,30 | 4,68 | 8,14 | 59,22 | 4,47 | 8,16 |
| 77 0318 | 4-O-CH$_2$-C$_6$H$_4$-CN | C$_{18}$H$_{16}$N$_2$O$_4$ | 324,32 | 135 | 72 | 66,66 | 4,97 | 8,64 | 66,48 | 4,84 | 8,75 |
| 77 0222 | 4-O-CH$_2$-C$_6$H$_4$-CN | C$_{18}$H$_{16}$N$_2$O$_4$ | 324,32 | 138 | 78 | 66,66 | 4,97 | 8,64 | 66,48 | 4,94 | 8,57 |
| 77 0569 | 4-OCH$_2$-C$_6$H$_4$-NH CO CH$_3$ | C$_{19}$H$_{20}$N$_2$O$_5$ | 356,37 | 212 | 50 | 64,03 | 5,66 | 7,86 | 64,33 | 5,69 | 7,79 |
| 77 0263 | 4-O-CH$_2$-C$_6$H$_3$-Cl$_2$ | C$_{17}$H$_{15}$Cl$_2$NO$_4$ | 368,21 | 140 | 40 | 55,45 | 4,11 | 3,80 | 55,66 | 4,13 | 3,68 |
| 77 0354 | 4-O-CH$_2$-C$_6$H$_3$-Cl$_2$ | C$_{17}$H$_{15}$Cl$_2$NO$_4$ | 368,21 | 138 | 36 | 55,45 | 4,11 | 3,80 | 55,70 | 4,19 | 3,84 |
| 77 0416 | 4-O-CH$_2$-C$_6$H$_3$-Cl$_2$ | C$_{17}$H$_{15}$Cl$_2$NO$_4$ | 368,21 | 135 | 25 | 55,45 | 4,11 | 3,80 | 55,43 | 4,12 | 3,75 |
| 77 0572 | 4-OCH$_2$-C$_6$H$_3$-Cl,F | C$_{17}$H$_{15}$ClFNO$_4$ | 351,75 | 110 | 50 | 58,04 | 4,30 | 3,98 | 57,83 | 4,21 | 3,88 |

TABLE I-continued $$\text{(I)}$$

Structure: phenyl ring with R substituent, N connected to oxazolidinone ring with CH2-OH group

| Code number | R | Empirical formula | Molecular weight | Melting point (°C.) | Yield (%) | Calculated (%) C | H | N | Obtained (%) C | H | N |
|---|---|---|---|---|---|---|---|---|---|---|---|
| 77 0672 | 4-OCH2-(2-NO2,4-Cl-phenyl) | C17H15ClN2O6 | 378,76 | 132 | 75 | 53,90 | 3,99 | 7,40 | 53,97 | 3,80 | 7,41 |
| 77 0790 | 4-OCH2-(2-Cl,4-NO2-phenyl) | C17H15ClN2O6 | 378,76 | 114 | 22 | 53,90 | 3,99 | 7,40 | 54,27 | 3,76 | 7,49 |
| 77 0789 | 4-OCH2-(2-CN,4-F-phenyl) | C18H15FN2O4 | 342,32 | 93 | 49 | 63,15 | 4,42 | 5,18 | 63,54 | 4,58 | 8,23 |
| 77 0298 | 4-OCH2-(2-pyridyl) | C16H16N2O4 | 300,30 | 138 | 33 | 63,99 | 5,37 | 9,33 | 64,05 | 5,44 | 9,44 |
| 77 0221 | 4-OCH2-(3-pyridyl) | C16H16N2O4 | 300,30 | 162 | 42 | 63,99 | 5,37 | 9,33 | 64,08 | 5,59 | 9,63 |
| 77 0299 | 4-OCH2-(4-pyridyl) | C16H16N2O4 | 300,30 | 144 | 46 | 63,99 | 5,37 | 9,33 | 64,28 | 5,30 | 9,46 |
| 77 0673 | 4-OCH2-(2-thienyl) | C15H15NO4S | 305,34 | 153 | 70 | 59,00 | 4,95 | 4,59 | 59,01 | 4,93 | 4,52 |
| 77 0889 | 4-OCH2-(2-furyl) | C15H15NO5 | 289,28 | 162 | 48 | 62,28 | 5,23 | 4,84 | 62,26 | 5,12 | 4,52 |
| 76 0904 | 4-OCH2-OCH3 | C12H15NO5 | 253,25 | 110 | 32 | 56,91 | 5,97 | 5,53 | 56,87 | 6,04 | 5,48 |
| 75 0601 | 4-O(CH2)2-N(morpholino) | C16H22N2O5 | 322,35 | 121 | 40 | 59,61 | 6,88 | 8,69 | 59,67 | 6,88 | 8,43 |
| 77 0180 | 4-SO5H11 n | C15H21NO3S | 295,39 | 113 | 73 | 60,99 | 7,17 | 4,74 | 61,15 | 7,06 | 4,87 |
| 77 0845 | 4-O-CH2-(pyrazinyl) | C15H15N3O4 | 301,30 | 148 | 32 | 59,79 | 5,02 | 13,95 | 59,51 | 4,79 | 13,87 |
| 77 1181 | 3-Cl-phenyl-CH2-CH2- | C18H15ClNO3 | 331,79 | 123 | 62 | 65,16 | 5,47 | 4,22 | 65,29 | 5,76 | 3,92 |
| 77 1263 | 3-NO2-phenyl-O-CH2- | C17H16N2O6 | 344,31 | 142 | 44 | 59,30 | 4,68 | 8,14 | 59,44 | 4,38 | 7,99 |
| 77 1082 | isopentyl-O- | C15H21NO4 | 279,33 | 100 | 53 | 64,49 | 7,59 | 5,01 | 64,24 | 7,80 | 4,85 |
| 77 1246 | -C(CH3)2-(CH2)2-O- | C16H23NO4 | 293,35 | 92 | 22 | 65,50 | 7,90 | 4,78 | 65,53 | 8,12 | 4,64 |
| 77 1245 | cyclopentyl-CH2-CH2-O- | C17H23NO4 | 305,36 | 108 | 35 | 66,86 | 7,59 | 4,59 | 66,89 | 7,85 | 4,53 |

TABLE I-continued
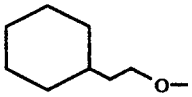 (I)
| Code number | R | Empirical formula | Molecular weight | Melting point (°C.) | Yield (%) | Calculated (%) C | H | N | Obtained (%) C | H | N |
|---|---|---|---|---|---|---|---|---|---|---|---|
| 77 0949 | 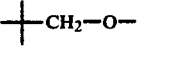 | C$_{18}$H$_{25}$NO$_4$ | 319,39 | 84 | 73 | 67,69 | 7,89 | 4,39 | 67,81 | 7,71 | 4,08 |
| 77 1249 | 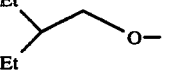 | C$_{15}$H$_{21}$NO$_4$ | 279,33 | 136 | 15 | 64,49 | 7,58 | 5,01 | 64,64 | 7,62 | 4,91 |
| 77 1197 | 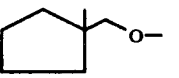 | C$_{16}$H$_{23}$NO$_4$ | 293,35 | 86 | 82 | 65,50 | 7,90 | 4,78 | 65,20 | 8,16 | 4,07 |
| 78 0076 | 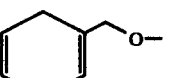 | C$_{17}$H$_{23}$NO$_4$ | 305,36 | 99 | 43 | 66,86 | 7,59 | 4,99 | 66,85 | 7,50 | 4,35 |
| 77 0984 | 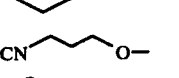 | C$_{17}$H$_{19}$NO$_4$ | 301,33 | 128 | 32 | 67,76 | 6,36 | 4,65 | 67,49 | 6,47 | 4,40 |
| 78 0259 | 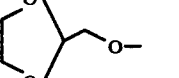 | C$_{14}$H$_{16}$N$_2$O$_4$ | 276,28 | 94 | 55 | 60,86 | 5,84 | 10,14 | 60,66 | 5,85 | 9,98 |
| 77 0962 | 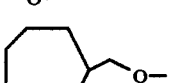 | C$_{14}$H$_{17}$NO$_6$ | 295,28 | 154 | 62 | 56,94 | 5,80 | 4,74 | 56,93 | 5,91 | 4,80 |
| 78 0030 |  | C$_{18}$H$_{25}$NO$_4$ | 319,39 | 111 | 80 | 67,68 | 7,89 | 4,39 | 67,76 | 8,12 | 4,07 |
| 78 0080 | 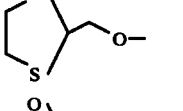 | C$_{14}$H$_{17}$NO$_4$S$_2$ | 327,42 | 160 | 60 | 51,35 | 5,23 | 4,28 | 51,51 | 5,28 | 4,00 |
| 78 0112 | 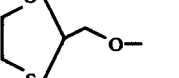 | C$_{14}$H$_{17}$NO$_5$S | 311,35 | 118 | 55 | 54,00 | 5,50 | 4,50 | 54,13 | 5,52 | 4,38 |
| 77 0900 | 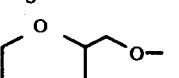 | C$_{16}$H$_{21}$NO$_5$ | 307,34 | 130 | 65 | 62,52 | 6,89 | 4,56 | 62,46 | 7,21 | 4,87 |
| 77 1301 | 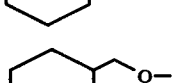 | C$_{16}$H$_{21}$NO$_5$ | 307,34 | 160 | 72 | 62,52 | 6,89 | 4,56 | 62,29 | 7,02 | 4,43 |
| 77 1240 | 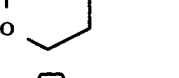 | C$_{17}$H$_{16}$IN$_2$O$_4$ | 314,33 | 132 | 88 | 64,95 | 5,77 | 8,91 | 64,71 | 6,00 | 8,71 |
| 77 1321 | 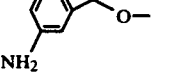 | C$_{17}$H$_{16}$INO$_4$ | 425,21 | 145 | 76 | 48,02 | 3,79 | 3,29 | 47,85 | 3,56 | 3,45 |
| 78 0182 | 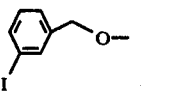 | C$_{19}$H$_{20}$N$_2$O$_6$ | 372,37 | 202 | 47 | 61,28 | 5,41 | 7,52 | 60,71 | 5,72 | 7,94 |
| 78 0443 | EtCONH—⟨phenyl⟩—CH$_2$—O— | C$_{20}$H$_{22}$N$_2$O$_5$ | 370,39 | 208 | 32 | 64,85 | 5,98 | 7,56 | 64,78 | 6,04 | 7,70 |

TABLE I-continued

Formula (I):
$$R\text{-}C_6H_4\text{-}N(\text{-}CH_2OH)\text{-}C(=O)\text{-}O\text{-}$$ (oxazolidinone with CH₂OH and N-aryl)

| Code number | R | Empirical formula | Molecular weight | Melting point (°C.) | Yield (%) | Calc. C | Calc. H | Calc. N | Obt. C | Obt. H | Obt. N |
|---|---|---|---|---|---|---|---|---|---|---|---|
| 77 0955 | O₂N—, F—, —CH₂O— (substituted benzyl) | C₁₇H₁₅FN₂O₆ | 362,31 | 110 | 82 | 56,35 | 4,17 | 7,73 | 56,16 | 4,40 | 7,43 |
| 77 1125 | O₂N—, CN—, —CH₂O— | C₁₈H₁₅N₃O₆ | 369,32 | 176 | 85 | 58,53 | 4,09 | 11,38 | 58,03 | 3,85 | 11,37 |
| 77 1199 | NO₂—, Cl—, —CH₂O— | C₁₇H₁₅ClN₂O₆ | 378,76 | 178 | 78 | 53,90 | 3,99 | 7,40 | 53,47 | 3,90 | 6,72 |
| 77 0979 | furyl-CH₂O— | C₁₅H₁₅NO₅ | 289,28 | 131 | 47 | 62,28 | 5,23 | 4,84 | 61,98 | 5,22 | 4,72 |
| 77 1067 | thienyl-CH₂O— | C₁₅H₁₅NO₄S | 305,34 | 144 | 23 | 59,00 | 4,95 | 4,59 | 59,04 | 4,98 | 4,43 |
| 78 0077 | dithianyl-CH₂O— | C₁₅H₁₉NO₄S₂ | 341,44 | 142 | 58 | 52,76 | 5,61 | 4,10 | 52,98 | 5,85 | 4,02 |
| 78 0562 | —O—(CH₂)₃—CN | C₁₅H₁₈N₂O₄ | 290,31 | 68 | 35 | 62,05 | 6,25 | 9,65 | 61,75 | 6,25 | 9,70 |
| 78 0564 | C₆H₅—CH=CH— (trans) | C₁₈H₁₇NO₃ | 295,32 | 215 | 71 | 73,20 | 5,80 | 4,74 | 72,92 | 5,72 | 4,66 |

The compounds of formula (I) were studied on laboratory animals and showed activities in the psychotropic field, as potential anti-depressants.

These activities were revealed in the following tests:

Test A: Potentiation in mice of generalized trembling caused by an interperitoneal injection (200 mg/kg) of dl-5-hydroxytryptophane, following the protocol described by C. Gouret and G. Raynaud in J. Pharmacol. (Paris), (1974) 5, 231.

Test B: Antagonism with respect to the ptosis observed one hour after an intravenous injection (2 mg/kg) of reserpine given to mice, following the protocol described by C. Gouret and J. Thomas in J. Pharmacol. (Paris), (1973), 4, 401.

Test C: Reduction in the density of pontogeniculo-occipital points (P.G.O.) caused by an intravenous injection (0.5 mg/kg) of reserpine given to cats, following the protocol described by A. Coston and C. Gouret in J. Pharmacol. (Paris) (1976), 7, 409.

The results of these three tests, as well as those of a well-known reference substance, TOLOXATONE, are collected, in Table II below:

TABLE II

| Compounds tested | Test A ED 50 (mg/kg/p.o.) | Test B ED 50 (mg/kg/p.o.) | Test C ED 50 (mg/kg/i.p.) |
|---|---|---|---|
| (a) Of the invention | | | |
| 770 365 | 29 | 25 | — |
| 770 423 | 35 | 25 | 5 |
| 770 152 | 20 | 25 | 15 |
| 770 696 | 15 | 20 | — |
| 770 388 | 9 | 12;5 | 4;5 |
| 770 788 | 6;25 | 12;5 | — |
| 770 467 | 2;8 | 1;2 | 3 |
| 770 466 | 9;6 | 6;2 | 9 |
| 770 196 | 20 | 15 | 16 |
| 770 154 | 50 | 50 | 20 |
| 770 131 | 2;5 | 3 | 5;5 |
| 770 126 | 8 | 11 | 16;5 |
| 760 904 | 50 | 50 | 8;5 |
| 750 601 | 70 | 8 | 31 |
| 770 180 | 35 | 45 | 45 |
| 770 501 | 22 | 25 | — |
| 770 328 | 25 | 35 | — |
| 770 155 | 50 | 22;5 | 35 |
| 770 230 | — | 6;25 | 16 |
| 770 231 | 40 | 50 | 14 |
| 760 557 | 7;3 | 3;3 | 110 |
| 770 234 | 1;5 | 0;7 | 9 |
| 770 318 | 25 | 16 | — |
| 770 222 | 2;8 | 1;2 | 5;2 |
| 770 569 | 5 | 2;5 | 6 |
| 770 268 | 7 | 8;5 | — |
| 770 354 | 25 | 30 | 30 |
| 770 416 | 6;2 | 10 | 3 |
| 770 572 | 6;3 | 3;12 | 8;5 |
| 770 672 | 25 | 19 | — |
| 770 790 | 50 | 25 | — |

TABLE II-continued

| Compounds tested | Test A ED 50 (mg/kg/p.o.) | Test B ED 50 (mg/kg/p.o.) | Test C ED 50 (mg/kg/i.p.) |
|---|---|---|---|
| 770 789 | 3 | 2 | — |
| 770 298 | 55 | 12;5 | — |
| 770 221 | 11;8 | 3;12 | 15 |
| 770 299 | 20 | 12;5 | — |
| 770 673 | 16 | 35 | 8 |
| 770 845 | 6;25 | 12;5 | — |
| 771 181 | 6;25 | 6;25 | — |
| 771 263 | 4 | 3;1 | — |
| 771 082 | 1;3 | 0;7 | — |
| 771 246 | 17 | 23 | — |
| 771 245 | 1;5 | 2 | — |
| 770 949 | 10 | 16 | — |
| 771 249 | 22;5 | 50 | — |
| 771 197 | 25 | 16 | — |
| 780 030 | 3 | 5;3 | — |
| 780 076 | 2;3 | 7 | — |
| 770 984 | 10 | 25 | — |
| 780 259 | 1;25 | 3;2 | — |
| 770 962 | 26 | 50 | — |
| 780 080 | 50 | 50 | — |
| 780 112 | 5 | 5;2 | — |
| 770 900 | 50 | 25 | — |
| 780 034 | 4;4 | 6;2 | — |
| 771 301 | 1;9 | 3 | — |
| 771 240 | 35 | 50 | — |
| 771 321 | 25 | 20 | — |
| 780 182 | 40 | 25 | — |
| 780 443 | 3;7 | 12;5 | — |
| 770 955 | 13 | 7 | — |
| 771 125 | 3;12 | 1;56 | — |
| 771 199 | 1;1 | 0;8 | — |
| 780 562 | 0;8 | — | — |
| 770 979 | 14 | 35 | — |
| 771 067 | 7;5 | 12;5 | — |
| 780 077 | 25 | 44 | — |
| (b) Reference | | | |
| TOLOXATONE | 60 | 50 | 28 |

As can be seen from the preceding results and those given in Table III below, the difference between the lethal doses and the pharmacologically active doses is sufficient for the compounds of the invention to be used in therapeutics.

TABLE III

| | Acute toxicity in mice | | |
|---|---|---|---|
| Compounds tested | Dose administered (mg/kg/p.o.) | Mortality (%) | LD 50 (mg/kg/p.o.) |
| (a) Of the invention | | | |
| 770 131 | 1000 | 0 | — |
| 770 222 | 1000 | 0 | — |
| 770 234 | 1000 | 0 | — |
| 760 652 | 1000 | 0 | — |
| 760 557 | 1000 | 0 | — |
| 771 082 | — | — | >2000 |
| 771 245 | — | — | >2000 |
| 771 301 | — | — | >2000 |
| 770 955 | 2000 | 17 | — |
| (b) Reference | | | |
| TOLOXATONE | — | — | 1850 |

As can be seen from the results shown in the preceding tables, the compounds of formula (I) have an activity greater than or equal to that of the reference compound.

They are indicated in endogenous and exogenous depressive conditions and will be administered orally in the form of tablets, pills or capsules, at a dosage of 500 mg/day on average, of active substance.

They will also be administered in the form of an injectable aqueous solution at the rate of 5–50 mg/day of active substance, the solvent used being formed by binary or ternary mixtures containing for example water, polypropyleneglycol or polyethyleneglycol (quality: 300–400), or any other physiologically acceptable solvent; the relative proportions of the different solvents being adjusted with respect to the dose administered.

What we claim is:

1. A compound having the formula

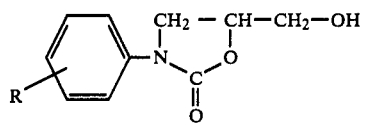

in which R is selected from the group consisting of:
a group having the formula

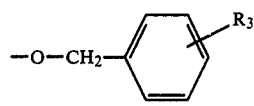

situated in para position and in which $R_3$ is selected from the group consisting of 2-cyano, 3-chloro, 3-bromo, 3-nitro, 3-cyano, 4-acetamido and 4—$NHCOC_2H_5$; and a group having the formula

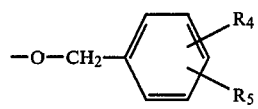

situated in para position and in which the combination of ($R_4$, $R_5$) is selected from the group consisting of (3—Cl, 4—Cl), (3—Cl, 5—Cl), (3—Cl, 4—F), (3—$NO_2$, 4—Cl), (3—CN, 4—F), (3—$NO_2$, 4—F), (3—$NO_2$, 5—CN) and (3—$NO_2$, 5—Cl).

2. A compound as claimed in claim 1 in which R is

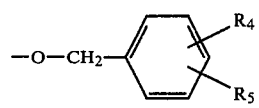

3. A compound as claimed in claim 2 in which R is

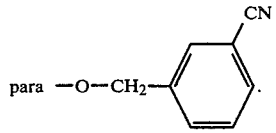

4. A compound as claimed in claim 2 in which R is

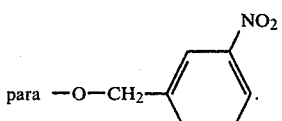

5. A compound as claimed in claim 1 in which R is

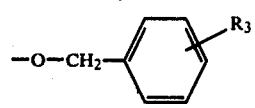
6. A compound as claimed in claim 5 in which R is
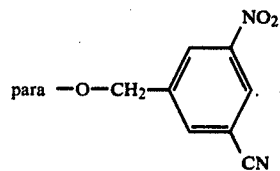
7. A compound as claimed in claim 5 in which R is
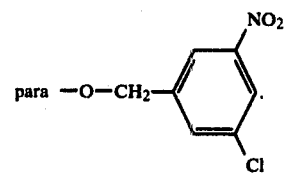
8. A compound as claimed in claim 5 in which R is
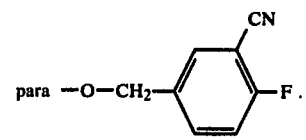
* * * * *

UNITED STATES PATENT OFFICE
CERTIFICATE OF CORRECTION

Patent No. 4 250 318           Dated February 10, 1981

Inventor(s) Philippe L. Dostert et al

It is certified that error appears in the above-identified patent and that said Letters Patent are hereby corrected as shown below:

Please change the name of the fourth inventor from "Claude G. Gouret" to ---Claude J. Gouret---.

Column 24, lines 45-50;   delete the formula and replace by

Column 25, lines 1-5;   delete the formula and replace by

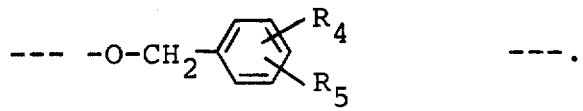

Signed and Sealed this

Sixteenth Day of June 1981

[SEAL]

Attest:

RENE D. TEGTMEYER

Attesting Officer    Acting Commissioner of Patents and Trademarks